(12) United States Patent
Mitarai

(10) Patent No.: US 9,491,949 B2
(45) Date of Patent: Nov. 15, 2016

(54) METHOD FOR RAISING PLANTS AND COMPOSITION USED THEREFOR

(75) Inventor: Kaoru Mitarai, Saiki (JP)

(73) Assignee: Meisho Co. Ltd., Oita (JP)

( * ) Notice: Subject to any disclaimer, the term of this patent is extended or adjusted under 35 U.S.C. 154(b) by 130 days.

(21) Appl. No.: 14/003,884

(22) PCT Filed: Mar. 12, 2012

(86) PCT No.: PCT/JP2012/056316
§ 371 (c)(1),
(2), (4) Date: Nov. 14, 2013

(87) PCT Pub. No.: WO2012/124665
PCT Pub. Date: Sep. 20, 2012

(65) Prior Publication Data
US 2014/0059720 A1    Feb. 27, 2014

Related U.S. Application Data

(60) Provisional application No. 61/451,782, filed on Mar. 11, 2011.

(51) Int. Cl.
*A01N 63/02*    (2006.01)
*C05F 11/08*    (2006.01)

(52) U.S. Cl.
CPC ............... *A01N 63/02* (2013.01); *C05F 11/08* (2013.01)

(58) Field of Classification Search
None
See application file for complete search history.

(56) References Cited

U.S. PATENT DOCUMENTS

| 6,406,690 B1 | 6/2002 | Peleg et al. |
| 6,808,917 B1 | 10/2004 | Johnson |
| 8,454,979 B2 | 6/2013 | Mitarai et al. |
| 2008/0274888 A1* | 11/2008 | Goldstein ............... A01N 37/46 504/149 |

FOREIGN PATENT DOCUMENTS

| CA | 2257371 A1 | 10/1998 |
| JP | 2911076 B2 | 4/1999 |
| JP | 2004-91425 A | 3/2004 |
| JP | 2008-538566 A | 10/2008 |
| WO | 2006-132712 A2 | 12/2006 |
| WO | 2010-095463 A1 | 8/2010 |

OTHER PUBLICATIONS

Roby et al. "Chitin Oligosaccharides as Elicitors of Chitinase Activity in Melon Plants" (1987), Biochemical and Biophysical Research Communications, vol. 143, No. 3: 885-892.*
Smith et al. "Autolysins of Bacillus subtilis: multiple enzymes with multiple functions" (2000), Microbiology, vol. 146: 249-262.*
Extended European Search Report for EP Patent Application No. 12757705.4, Sep. 11, 2014. (6 pages).
Stachelhaus T, et al., Peptide Bond Formation in Nonribosomal Peptide Biosynthesis, The Journal of Biological Chemistry, vol. 273 (1998) 22773-22781.
Gruenewald S, et al., In Vivo Production of Artificial Nonribosomal Peptide Products in the Heterologous Host *Escherichia coli*, Applied and Environmental Microbiology, 70 (2004) 3282-3291.
2nd Office Action for EP Patent Application No. 12757705.4, mailed Apr. 18, 2016 (8 pages).
Ahmed I, et al., "Proposal of *Lysinibacillus boronitolerans* gen. nov. sp. nov., and transfer of *Bacillus fusiformis* to *Lysinibacillus fusiformis* comb. nov. and *Bacillus sphaericus* to *Lysinibacillus sphaericus* comb. nov." , International Journal of Systematic and Evolutionary Microbiology. vol. 57, May 1, 2007. pp. 1117-1125. XP055264621, GB, ISSN: 1466-5026, DOI: 10.1099/ijs.0.63867-0.
Setlow, Peter, "Spore germination", Current Opinion in Microbiology, vol. 6, No. 6, Dec. 1, 2003, pp. 550-556, XP055056665, ISSN: 1369-5274, DOI: 10.1016/j.mib.2003.10.001.
El-Banna, Nasser M, "Antifungal activity of Comamonas acidovorans isolated from water pond in south Jordan", African Journal of Biotechnology, Oct. 4, 2007, pp. 2216-2219, XP055264623, Victoria Island, DOI: 10.55897/ AJB2007.000-2347 [retrieved on Apr. 12, 2016].
Okamura, Kazuhiko, et al., " PS-5, Anew Beta-Lactam Antibiotic", The Journal of Antibiotics, Mar. 29, 1979, XP055264624.
Sgroy, Veronica, et al., "Isolation and characterization of endophytic plant growth-promoting (PGPB) or stress homeostasis-regulating (PSHB) bacteria associated to the halophyte *Prosopis strombulifera*", Applied Microbiology and Biotechnology, Springer, Berlin, DE, vol. 85, No. 2, Aug. 5, 2009, pp. 371-381, XP019757465, ISSN: 1432-0614, DOI: 10.1007/S00253-009-2116-3.

* cited by examiner

*Primary Examiner* — Robert Yamasaki
*Assistant Examiner* — Teresa E Knight
(74) *Attorney, Agent, or Firm* — Haynes and Boone, LLP

(57) ABSTRACT

To provide a method for raising plants that have great vitality and that are strongly resistant to pests and can successfully compete against weeds. The invention provides a method for raising plants with enhanced immunity and biological activity to external and internal stresses. The present invention is characterized by the following: the method includes a step of applying to the target plants a plant immunopotentiating composition containing an immunostimulatory substance produced by the cytolysis that accompanies spore formation in aerobic endospore-forming bacteria; the immunostimulatory substance is obtained by culturing the aerobic endospore-forming bacteria, causing the bacteria to form endospores by placing the resulting culture liquid in starvation conditions, and then removing impurities including the bacterial cells that are formed into endospores from the culture liquid; and the aerobic endospore-forming bacteria belong to the MRE symbiotic bacteria group.

10 Claims, 4 Drawing Sheets

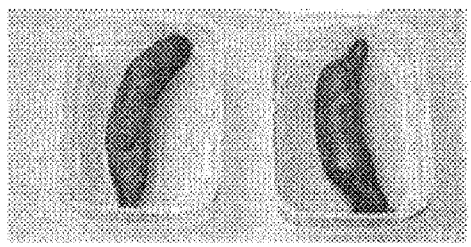
a  FIG. 2A
b  FIG. 2B
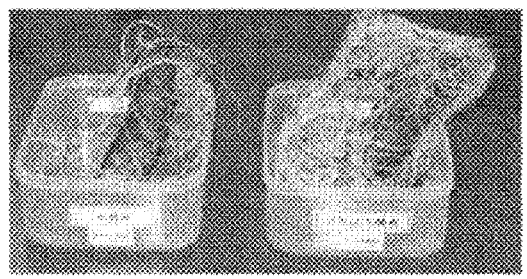
c  FIG. 2C

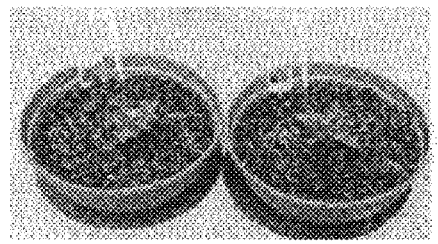
a  FIG. 3A
b  FIG. 3B
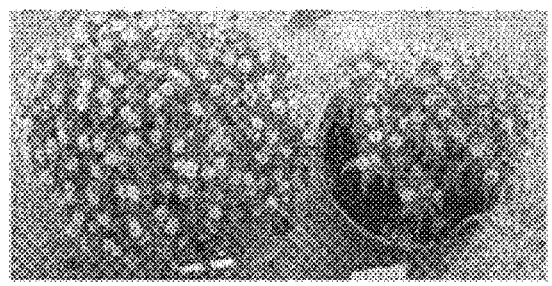
c  FIG. 3C

METHOD FOR RAISING PLANTS AND COMPOSITION USED THEREFOR

CROSS REFERENCE TO RELATED APPLICATIONS

This application is a United States national phase of co-pending international patent application No. PCT/JP2012/056316, filed Mar. 12, 2012, which claims benefit of U.S. provisional application No. 61/451,782, filed Mar. 11, 2011, the disclosure of which are incorporated herein by reference.

FIELD OF THE INVENTION

The present invention relates to a method for growing plants and composition material that is used for the methods. In particular, the present invention relates to a natural farming method where no fungicides for agriculture, pesticides, or herbicides are used.

BACKGROUND OF THE INVENTION

Conventionally, as farming methods of minimally using fungicides, insecticides, or herbicides, various farming methods including organic framing which mainly uses compost, EM farming which attempts to improve soil bacteria, and farming of genetically modifying spices, have been developed by repetition of researches. Reasons for developing organic farming methods are to protect agricultural workers' health and to protect consumers from contaminated food.

Because an organic farming method uses excessive amount of nutrition containing nitrogen, the crop is susceptible to disease and insect pest, and because weeds often dominate the farming field, it is difficult to adopt the farming method without using fungicides, pesticides, and herbicides. Although the natural cultivation where various plants including weeds coexist made possible to produce natural and delicious crop without giving any fertilizer by virtue of nutrition that natural microorganisms and roots of other plants produce without pesticide, it was the problem that the yield is low while the work is very time-consuming. In addition, the natural cultivation requires deep specialized knowledge such as know-how of a combination of vegetation.

Furthermore, in organic farming, for example, as patent articles 1 and 2 disclose, there are several improvements for increasing food safety by employing fermented compost similar to a natural product, and spraying an antibacterial agent made from natural objects on the plant leaves. However, they are merely means for protecting plants from microbes or nurturing plants from the outside, not enhancing the plant's vitality. In other words, these farming methods did not provide means for acquiring pathogen-resistance, vermin-resistance, and weed-resistance by strengthening plant's life.

On the other hand, in a farming method, called the natural cultivation method, a period of five years or longer is required for getting natural cultivation be ready, and highly advanced knowledge and skills including the vegetation strategy, the weed treatment, and the disease and pest control are required. What is more, there is also a problem that the yield is low for much labor, resulting in small production of expensive crops.

In addition, these techniques of the prior art did not use activity of innate immunity intentionally and intensively.

REFERENCE ARTICLE IN PRIOR ART

Patent Documents

Patent document 1: Japanese Patent No. 2911076.
Patent document 2: Japanese Laid-Open Patent Publication No. 2004-91425

Non-Patent Documents

Non-patent document 1: Stachelhaus T, et al., J. Biol. Chem., 273 (1998) 22773-22781
Non-patent document 2: Gruenewald S, et al., Appl. Environ. Microbiol., 70 (2004) 3282-3291

SUMMARY OF THE INVENTION

Considering the above technological problems, the purpose of the present invention is to provide a method for growing plants with strong vitality to compete with weeds, disease and pests. Another purpose of the present invention is to provide a method for growing plants whose productive yield is large even without resorting to compost (the innate immune activation farming method).

Furthermore, another purpose of the present invention is to provide a cultivating plant with resistance to salt and herbicide by the method of the present invention (i.e., the innate immune activation farming method).

The present invention is based on the discovery that immunopotentiating composition provides plants with resistance for various stresses, and effectively solves the aforementioned problem. Giving the immunopotentiating composition to plants including horticultural and agricultural plants, and fruit trees, not only enhances the resistance to pests, but also activates photosynthesis more, which grows their roots more and forms a strong biofilm on the roots to absorb nutrients, and promotes physiological activity of the plants.

Therefore, according to the primary aspect of the present invention, it is to provide a method for growing plants which have enhanced immunity or physiological activity to internal or external stress, comprising: a step of applying a plant immunopotentiating composition which contains an immunostimulatory substance produced in cell lysis associated with spore formation of spore aerobic bacteria to a plant, wherein the immunostimulatory substance is obtained by incubating the spore aerobic bacteria, placing a resultant culture medium under a starvation condition, thereby causing the bacteria to internally sporulate, and removing from said culture medium impurities containing said internally sporulated bacteria, and the spore aerobic bacteria is an MRE symbiotic bacteria group.

According to the above configuration, it is possible to provide a plant with enhanced intrinsic bioactivity. According to the present invention, it is possible to enhance antimicrobial, antiviral, and antifungal activities by virtues of the innate immunity of the plant, and furthermore, it is possible to promote photosynthesis and the activity of mitochondria by activating the vacuolar autophagy. Because of this enhancement, it is possible to grow plants that have more bioactivity while minimizing the supply of nutrients from the outside.

According to an embodiment of the present invention, the step of applying is spraying the plant immunopotentiating composition on either soil or cultivation medium for plants so that the immunopotentiating composition is absorbed by plant roots.

According to another embodiment of the present invention, the step of applying is applying the plant immunopotentiating composition onto the leaves of the plant.

According to another embodiment of the present invention, in the method, the plant acquires a trait selected from a group consisting of anti-pathogenic activity, anti-pest activity, salt tolerance, and herbicide resistance.

According to yet another embodiment of the present invention, in the method, the internal or external stress is selected from a group consisting of pathogenic, pests, viruses, high concentration of salt, strong light, ultraviolet radiation, high temperature, low temperature, dryness, heavy metals, and air-polluting gas.

According to yet another embodiment of the present invention, in the method, the plant is selected from a group consisting of leafy vegetables, flower bud vegetables, bulb vegetables, stem vegetables, seed vegetables, root vegetables, plants which give beans or grain, plants which give fruits, plants which to give ornamental flowers, and medical plants. In this case, the plant is preferably selected from a group consisting of rice, sweet potato, Million Gold, Gloxinia, orange, tomatoes, apple, leek onions, lotus root, okra, red beans, Sasagi, soybean, taro, potato, snack peas, green pepper, green onion, cucumber, eggplant, purple vine vegetables, bitter gourd, persimmons, ginger, butterbur, plum, blueberry, Popo, pepper, radish, turnip, broccoli, mizuna, Chinese cabbage, and broad beans.

Furthermore, according to yet another embodiment of the present invention, in the method, the plant immunopotentiating composition is diluted in the range from 100 to 1000 times.

According to another embodiment of the present invention, the step of the applying is carried out once every 1 to 3 weeks.

According to another embodiment of the present invention, in the method, the plant is grown in a form selected from a group consisting of upland, paddy, hydroponics, natural cultivation, and greenhouse cultivation.

According to the second major aspect of the present invention, a plant grown by the method described above is provided.

In addition, according to the third main aspect of the present invention, the plant immunopotentiating composition for growing plants which have enhanced immunity or physiological activity to internal or external stress, comprising an immunostimulatory substance produced in cell lysis associated with spore formation of spore aerobic bacteria to a plant, wherein the immunostimulatory substance is obtained by incubating the spore aerobic bacteria, placing a resultant culture medium under a starvation condition, thereby causing the bacteria to internally sporulate, and removing from said culture medium impurities containing said internally sporulated bacteria, and the spore aerobic bacteria is an MRE symbiotic bacteria group.

According to an embodiment of the present invention, the plant which uses the composition acquires a trait selected from a group consisting of anti-pathogenic activity, anti-pest activity, salt tolerance, and herbicide resistance.

According to another embodiment of the present invention, the composition is diluted in the range from 100 to 1000 times.

According to the fourth major aspect of the present invention, a fertilizer comprising the aforementioned composition is provided.

Furthermore, according to the fifth major aspect of the present invention, soil comprising the aforementioned composition is provided.

Furthermore, according to the sixth main aspect of the present invention, a plant cultivation kit comprising plant seeds and the aforementioned composition is provided.

Referring to the embodiments and the following drawings of the present invention, characteristics, operation and effect other than described above become clear to those skilled in the art.

BRIEF DESCRIPTION OF THE DRAWINGS

FIG. 2 shows a photograph to compare the growth of sweet potato with and without using the plant immunopotentiating composition in an embodiment of the present invention.

FIG. 3 shows a photograph to compare the development of Million gold with and without using the plant immunopotentiating composition in an embodiment of the present invention.

DETAILED DESCRIPTION OF THE INVENTION

Figures 1A, 1B:
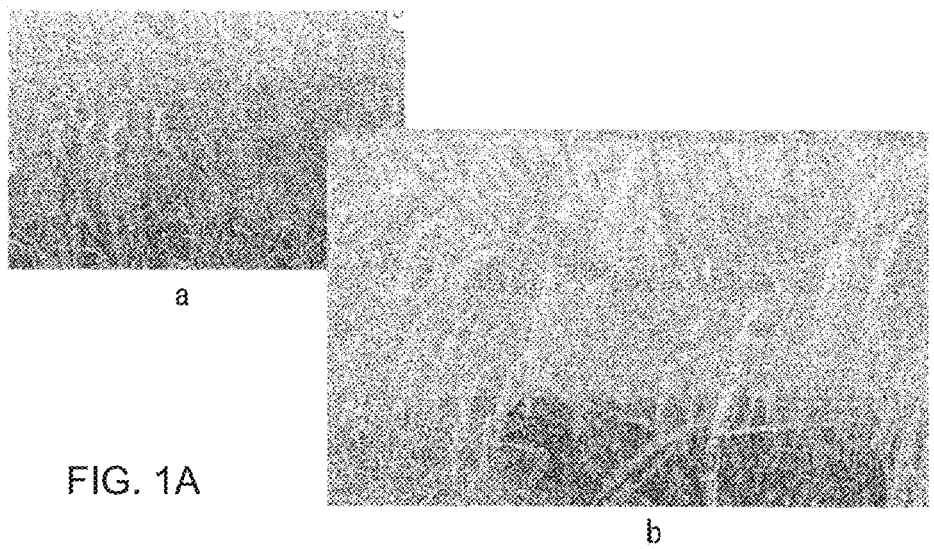
FIG. 1 shows a photograph to compare the cultivation of rice with and without using the plant immunopotentiating composition in an embodiment of the present invention.

Referring to the figurers, an embodiment of the present invention will be described in detail hereafter.

In the present invention, at the plant cell level, it is believed that innate immunity associated with the immunopotentiating composition which is obtained by a series of activities of culturing the aerobic endospore-forming bacteria, causing the bacteria to form endospores by placing the resulting culture liquid in starvation conditions, and then removing impurities including the bacterial cells that are formed into endospores from the culture liquid, activates vacuolar autophagy closely correlated with innate immunity at the molecular level. Vacuole of a plant is one of the intracellular organs that are known to have a function of detoxicating cells, and it also has another function of transferring to the vacuole is wrapped, bulk decomposition with the processing enzyme, which is a special enzyme vacuoles. Because plants perform photosynthesis with sunlight which contains strong ultraviolet, organelles including mitochondria and chloroplasts are damaged by continuous exposure to free radicals, e.g., singlet oxygen, caused by sunlight, and the vacuole autophagy is vital to reproduce organelles by decomposing the dilapidated intracellular substance. Because the free radicals oxidize the intracellular substance to change it toxins for the biological system, antioxidants such as the polyphenol are secreted in the vacuole in order to detoxicate these oxidation poisons.

In other words, in the present invention, by the action of the aforementioned plant immunopotentiating composition, the vacuole autophagy closely related with the innate immunity at the molecular level is activated. The vacuole autophagy transfers dilapidated chloroplast (cell organelles responsible for photosynthesis) or dilapidated mitochondria (cell organelles responsible for photosynthesis), wrapped with a special membrane (Auto phagocytosis Sohm) to the vaculose where the string processing enzyme decompose the transferred substance. Then, as described above, by decomposing mitochondria and chloroplasts damaged by free radicals, mitochondria or chloroplasts are reproduced and rejuvenated, which activates photosynthesis.

The organic components, including the sugar made in the photosynthesis, are sent to the plant root along with oxygen to promote growing the plant root. It is estimated that the plant immunopotentiating composition which has low molecular weight, neutral, and non-polar can be transferred from the leaves to the roots easily to activate the innate immunity.

The activated root cells actively secrete organic acids, sugar-degrading enzyme, and antibacterial substance. The secreted organic acid and other substances may produce plant nutrition by dissolving insoluble phosphorus compound and potassium salt existing abundantly in soil. For example, the pine root is known that it can dissolve rocks.

The plant root creates immune defense by releasing various antibacterial substances and the degrading enzyme against harmful soil bacteria while forming a biofilm to wrap the plant root by providing beneficial bacteria with sugar and oxygen. Because many nitrogen-fixing bacteria groups are getting discovered, the biofilm produced by the useful bacteria in the plant root may be attributed to acquisition of nitrogen component by root.

Thus, production of a nutrient phosphate, potassium and nitrogen by decomposing the insoluble nutrient in soil may reduce the amount of compost, and also be advantageous in competition with weeds.

In the method according to the present invention, the aforementioned plant immunopotentiating composition stimulates receptors which activate the innate immunity, including the toll like receptors (TLR) existing in the endosome or plasma membrane of the plant, the nod-like receptors (NLR) existing in the cytoplasmic in the cells, and the rig-like receptors (RLR). As the plant immunopotentiating composition, the present invention specifically uses low molecular decomposition products of inner spores which form a bacteria group consisting of Gram-negative bacteria and aerobic Gram-positive bacteria.

Here, the innate immunity refers to a mechanism where receptors of the innate immunity are stimulated by the aforementioned plant immunopotentiating composition to release antibacterial and antiviral substances. In addition, in the mechanism of the innate immunity of plants, the mechanism of autophagy using lysosomes or vacuoles which plays an important role in anti-aging and intracellular detoxification of plants, and the mechanism of apoptosis which plays an important role in forming antiviral an plant organs are closely related to the mechanism of the innate immunity at the molecular level. In other words, the innate immunity of a plant functions to protect itself from the foreign predators, i.e., bacteria, fungi, and viruses, and at the same time, in addition to the foreign enemies, it also protect itself from the internal enemies, i.e., anti-aging of the cells and detoxification in then cells.

As described above, in addition to increasing the resistance against bacteria, virus, and mold of plants, the innate immunity enhances the physiological activity of the plant by stimulating the functions of apoptosis and autophagy, rejuvenates itself by removing aged chloroplast and mitochondria by the vacuole autophagy, re-activating the photosynthesis. Hence, the aforementioned plant immunopotentiating composition has the function of increasing the vitality of the plant.

Specifically, since PCT/JP2010/001120 disclosed that the immunopotentiating composition described in the patent article has a remarkable function as innate immune ligands, a highly productive farming method closed to the natural growth (i.e., the innate immune activation farming method) has been achieved. Rather than farming methods of giving organic fertilizers and soil bacteria, the above farming method produces the necessary nutrition to overcome plant diseases by enhancing the vitality of agricultural crops. This method not only minimizes the amount of herbicides and pesticides but also produces fruits, grains, and vegetable which contain more sugar and acidity.

In addition, it was also discovered that the farming method using the plant immunopotentiating composition repelled pests. In other words, the cultivating plant does not absorb the nitrogen component excessively because the method of the present invention may minimize the amount of organic fertilizer. In general, pests are attracted to the nitrogen component secreted from the leaves of the crop, and therefore, there will be more damage caused by pests in a farming method to grow larger crops by giving a large amount of the nitrogen-rich organic fertilizer. However, because the farming method of the present invention suppresses use of organic fertilizers as much as possible, it is possible to reduce the pest damage.

Therefore, the farming method of the present invention may solve the problems described above; furthermore, the method of the present invention may adapt any agricultural form such as paddy, greenhouse cultivation, indoor hydroponics, nature cultivation, and kitchen garden; and organic cultivation, natural cultivation, hydroponics, and genetically modified crops may be applied as well.

As mentioned above, the present invention provides a method for growing plants which have various plant stress resistances and tolerance by utilizing the plant immunopotentiating composition. The aerobic bacterium is not particularly limited if it forms the inner spores, and is preferably selected from an MRE symbiotic bacteria group. Moreover, aerobic bacteria used in the method of the present invention may be a mixed bacterial group consisting of one or more aerobic bacteria.

Here, the MRE symbiotic bacteria group consist of *Bacillus* sp. (FERM BP-11209, the identification number MK-005), *Lysinibacillus fusiformis* (FERM BP-11206, the identification number MK-001), *Bacillus sonorensis* (the identification number MK-004), *Lysinibacillus* sp. (FERM BP-11207, the identification number MK-002), and *Comamonas* sp. (FERM BP-11208, the identification number MK-003), all of which are aerobic.

The method of the present invention filters the solution in which spores was formed and precipitated by using a membrane of pores size 0.2 μm and a filter of pores size 0.02 μm to remove small amount of residual cultured cells and endospores remaining suspended, and then the filtered solution is aerated, making plants be stress tolerant. The present inventors have found that which this solution is suitable for growing plants growth to realize the present invention.

The "plant immunopotentiating composition" of the present invention may be obtained by decomposing bacterial cells, such as aerobic Gram-positive bacteria and aerobic Gram-negative bacteria of low molecular weight less than 3000 Da (preferably in the range from 1000 Da to 300 Da) by using or mother cell lysis enzymes or lysosomal enzymes. In particular, the plant immunopotentiating composition produced by decomposing the MRE symbiotic bacteria group by using mother cytolytic enzymes of the MRE symbiotic bacteria group exhibits superior physiological activity in animals (human, in particular), and the present invention have discovered that it has a similar superior effect on plants.

The present invention performs the low molecule decomposition of bacteria by promoting the inner spores to induce the mother cell lysis enzymes in a cultured symbiotic bacteria which contain one or both of the aerobic Gram-negative bacteria and aerobic Gram-positive bacteria. More specifically, first, the culture solution of a single or mixed bacterial groups of aerobic Gram-negative bacteria and aerobic Gram-positive bacteria is prepared with the following cultural conditions: pH in the range from 6.0 to 6.8, the temperature in the range from 25° C. to 30° C., and the dissolved concentration in the range from 0.1 mg/L to 1.0 mg/L by aeration. The nutrition of bacteria such as minerals including silica and magnesium sulfate, fish meal, rice bran, dreg, and gravy. For a mixed bacterial group, and some time interval should be earned to establish a stable symbiosis of bacteria.

Once the culture of bacteria becomes stabilized, the bacteria group in the vegetative cell state is separated into another culture aeration tank for continuing the cell culture. While continuing the aeration in the culture aeration tank, then fractionated bacteria group is placed starved without all nutrition except silica. When remaining nutrition is exhausted, spore (inner sporulation) occurs to trigger depletion of the nitrogen component as the liquid becomes transparent. Upon confirming that the spores (inner spores), if the aeration (supplying oxygen) is stopped and the solution is left for a while, the spores precipitate simultaneously to obtain a clear supernatant. The supernatant is filtered through a membrane to obtain an innate immune ligand stock solution for plants. The filtered solution may be filtered through a filter of pores size 0.02 μm further as required.

The method according to the present invention may use any of the supernatant, the filtrate through the membrane, and the filtrate through the filter of size 0.02 μm.

The bacteria group is preferably the MRE symbiotic bacteria group which was disclosed in PCT/JP2010/001120 (MK-001, MK-002, MK003, MK-004, and MK-005) but it is not limited to the MRE symbiotic bacteria group.

In the aerobic Gram-positive bacteria, the following groups may be used: *Baccilus* genus, *Sporelactobacillus* genus, *Paenibacillus* genus, *Aneurinibacillus* genus, and *Oceanobacillus* genus of advanced salt alkalophilic; and soecuifically, a bacteria group, including *Bacillus alcel, Bacillus cirulans, Bacillus licheniformis, Bacillus megaterium, Bacillus pumilus, Bacillus* For more information subtillis, *Bacillus thuringiensis, Bacillus lentimorbus, Bacillus alvei, Bacillus macerans, Bacillus polymyxa, Bacillus popilliae, Bacillus coagulans, Bacillus stearothermophilus, Bacillus thermoruber, Bacillus acidocaldarius, Bacillus acidoterestris, Bacillus aycloheptainicus, Bacillus alginalyticus, Bacillus azotoforians, Bacillus badius, Bacillus pasteurii*, fungus group, including *Bacillus aminovrans, Bacillus marinus, Bacillus pusteurii, Bacillus sphaericus, Bacillus benzoevorans, Bacillus fastidiosus*, and *Bacillus nagunoensis*.

In the aerobic gram-negative bacteria, a fungus group having the properties of non-pathogenic spore aerobic Gram-negative bacteria such as the genus *Comamonas* may be used.

For example, if using the MRE symbiotic bacteria group, a culture solution, having volume 1 m³, of the MRE symbiotic bacteria group of aerobic bacteria which form the aforementioned inner spore (MK-001, MK-002, MK003, MK-004, and MK-005) is placed in each of the two identical culture aerating vessels of the same shape and volume of 1.2 m³, and the aeration to be a dissolved oxygen concentration of in the range from 0.5 mg/L to 1.2 mg/L is performed. One of the two tanks is called the spore vessel while the other is called the cell culture vessel. For the cell culture vessel, fish meal 500 g, rice bran 500 g, oil cake 250 g, gravy 50 g are added as the minimal nutrition, and aeration is continued under the culture condition of pH in the range from 6.0 to 6.8 and the incubation temperature in the range from 25° C. to 35° C. On the other hand, in the spore vessel, no nutrition is provided in starvation and the aeration is continued at the temperature in the range from 25° C. to 35° C. As the culture solution increases its transparency, the aeration (supplying oxygen) is stopped to let the inner spores precipitate at once and the solution becomes transparent. The transparent solution is filtered through a membrane of pores size 0.2 μm, then further filtered through a 0.02 μm filter, and the filtered solution is placed in the spore vessels which is re-cleaned well for preparing the resolving power test. Here, the filtered solution, the MRE symbiotic bacteria group spored solution from which the residual oocytes and spores are removed with the filters called the MRE filtrate. Therefore, although there are almost no fungi nor spores in the MRE filtrate, an immunopotentiating substance is present in the MRE filtrate. The present invention is intended to use this immunopotentiating substance. This specification may use the expressions such as the "MRE filtrate, "the solution after sporing," and "the solution without bacteria after sporing," they are all solutions which have a plant immunopotentiating composition unless otherwise noted.

The present invention does not particularly limit the pores sizes of the filter and the membrane. For example, the membrane of pores sizes 1 μm, 0.7 μm, 0.5 μm, even 0.3 μm may be sued, and preferably the size of 0.2 μm may be used. The filter may be pores sizes of 0.02 μm 0.15 μm, 0.1 μm, 0.07 μm, 0.05 μm, and 0.03 μm, preferably the size of 0.02 μm may be used.

In the present invention, while performing aeration through the spore vessel and the cell culture vessel maintain the dissolved oxygen concentration in the range from 0.5 mg/L to 1.2 mg/L, the following tests are conducted.

The plant immunopotentiating composition obtained in the manner described above is used by diluting the stock solution 100 to 1000 times depending upon the growth stage and the type of plant, but it is not particularly limited as long as the favorable effect is obtained. For example, it may be diluted 100 times, 200 times, 300 times, 400 times, 500 times, 600 times, 700 times, 800 times, 900 times, and 1000 times depending on the growth stage and the type of plant.

The method for applying the plant immunopotentiating composition to a plant may be absorption by spraying (coating) on leaves, disseminating on soil or a plant growing medium, and other methods but it is not particularly limited as long as it is a method for having plants absorb an appropriate amount and concentration of the immunopotentiating composition.

The number and frequency of application may be once every 1 to 3 weeks but may be adjusted appropriately, depending on the growth stage and the type of plant. For example, it is possible to be once every 2 to 3 days. Furthermore, at any growth stage from seeding to harvesting, the application may be done.

Dilution spraying concentrations for various plant species are listed as follows.

TABLE 1

| Plant | Concentration and dissemination method |
|---|---|
| Rice paddy and wheat, etc. | (1) Soak rice hulls in a solution diluted 200 times.<br>(2) In seed bed of 10 cm, spay solution diluted 300 to 500 times on the entire area when it grows.<br>(3) For rice, put 20 L/tan of undiluted solution to field when drawing water after rice-planting and heading.<br>(4) After heading, spray a solution diluted 200 to 300 times on leaves 1 to 2 times.<br>(5) For wheat, spray a solution diluted 200 to 300 times on leaves after treading wheat sprouts and heading. |
| Citrus and fruit | 1) Spray a solution diluted 200 times on leaves and stems after flowering, fertilization, and fruition. Repeat spay every 2 to 3 weeks until harvest.<br>2) After harvest, spray a solution diluted by 200 times on leaves and stems once.<br>3) Spray a solution diluted 200 to 300 times as required for root rot. |
| Greens (cabbage, Chinese cabbage, spinach, and mizuna, etc.) | 1) After heading, spray a solution diluted 300 to 500 times on whole plant.<br>2) After cropping, spray a solution diluted 200 to 300 times on whole plant.<br>3) Spray a solution diluted 200 to 300 times on whole plant every 1 to 2 weeks until harvest. |
| Seed vegetables (cucumber, eggplant, and pumpkin, etc.) | 1) After heading, spray a solution diluted 300 to 500 times on whole plant.<br>2) After potting, spay a solution diluted 200 to 300 times on whole plant.<br>3) When planting permanently, provide a solution diluted 100 times as water for groundwork.<br>4) Spray a solution diluted 200 to 300 times on whole plant every 1 to 2 weeks until harvest. |
| Strawberry, etc. | 1) While raising seedlings, spray a solution diluted 200 to 300 times on the whole plant.<br>2) Spray a solution diluted 200 to 300 times on the whole plant every 7 to 10 days.<br>3) When planting permanently, provide a solution diluted 100 times as water for groundwork.<br>4) Spray a solution diluted 200 to 300 times on whole plant every 1 to 2 weeks until harvest. |
| Root vegetables | 1) While raising seedlings, spray a solution diluted 200 to 300 times on the whole plant.<br>2) Spry a solution diluted 200 to 300 times on whole plant every 1 to 2 weeks until harvest. |
| Flowering trees | 1) Dilute the solution 200 to 1000 times, and spray the diluted solution on whole leaves every 2 to 3 weeks. |
| Tea | 1) Dilute the solution 2000 times and spray the diluted solution on the whole tree before shooting new sprouts, and after $1^{st}$, $2^{nd}$, and $3^{rd}$ tea crops. |
| Hydroponic culture | 1) Dilute the solution 500 to 1000 times and spry the diluted solution on leaves. |

Because the plant immunopotentiating composition sprayed in this manner is mostly nonpolar uncharged component of molecular weight 1000 Da or less, it may be absorbed easily from the surfaces of leaf and root. The absorbed plant immunopotentiating composition increases the innate immune activity of leaves and root to improve the stimulated emission powers of antibacterial, antiviral substance, and anti of such antifungal enzymes. Plants which have no phagocytic cells for immunization, such as neutrophils and macrophages, secrete a variety of antimicrobial substances. Plant defensins (antimicrobial peptides), lectin (linked to the sugar chain) anti-fungal degradation enzyme (such as chitin degrading enzyme and beta-glucan-degrading enzyme) are known as the antibacterial substance of plants.

For example, as being collectively referred to as phytoalexin, each of antibacterial substance called momilactone and Sakuranechin, 5 different phytocassanes, all of 7 different Orizarekishina, totally 15 different types have been discovered from the leaf of rice. In addition to the rice, and antibacterial substances of more than 250 different plants, including Guriseorin of soybean, Lisitsyn of potato, Pisachin pea, phaseolin of the common bean, allyl isothionates of radish, allicin in garlic, amygdalin of Rosaceae (which changes to prussic acid) are is known. Plants which have no dynamic innate immune system, such as phagocytes, including antimicrobials of small molecules, have the ability to secrete a variety of antimicrobials including antimicrobial peptides, lectins, and low molecular antimicrobials.

These antibacterial substances have a mechanism to secrete alarm substances including interferon alpha and interferon beta of animal by activating the innate immune sensor (receptor) which plants, animals, micro-organisms have in common, to inform adjacent cells. It is believed that many of the adjacent cells would release antibacterial antiviral substance or antifungal enzymes at once by sensing the secreted alarm substance. Among the innate immune sensors, there are the same innate immune sensors that have the same function, including toll like recepter (TLR) animal on the cel surface, nod like receptor (NLR) and RIG-I like receptor (RLR) inside the cell. For example, there have been found the innate immune sensors (receptors), such as FLS2, Xa21, CLV1-3, Aw9 in the cell membrane, and the innate immunity internal sensors (receptors), such as RPS2 and RPS4 inside the cell.

The plant immunopotentiating composition of the present invention stimulates the innate immune sensor (receptor) of cells of not only humans and animals but also leaves and roots of plants to activate the innate immunity. Because viruses, both DNA viruses and RNA viruses, penetrate into the gene inside animal cells for proliferation using the gene's mechanism, antibacterial substances such as natural antibodies and lectins and antimicrobial peptides cannot eliminate virus invaded into cells in. Animals, which have the natural killer cell which is a movable innate immune cell, the natural killer T cell, or the killer T cell (only in vertebrates) which is a lymphocyte immune cell, can induce apoptosis (or programmed natural death) of virus-infected cells while plants do not have the movable innate immune cells. For this reason, plant cells have the ability to cause apoptosis (suicide) of themselves with viruses. Because the innate immune closely relates to apoptosis through the molecular mechanism, the plant immunopotentiating composition may activate inducing apoptosis against viral infection.

In addition, because the innate immune also closely relates to the autophagy mechanism for intracellular detoxification through the molecular mechanisms, the plant immunopotentiating composition for increasing the innate immune activity may also increase the activity of vacuole autophagy of processing enzymes at the same time.

The vacuole autophagy in plants decomposes chloroplast and mitochondria of dilapidated plant cells. Due to this process, new normal chloroplasts and mitochondria are divided for replacement. This replacement rejuvenates the plant cells, activating the plant cells for photosynthesis to produce much nutrients such as sugar, which activates energy production and cell division in root and leaf and energy production of stems and leaves and roots become active nutrients such as sugar is produced in large amounts of photosynthesis function becomes active. By this rejuvenating dilapidated mitochondria and chloroplasts, the efficiency of photosynthesis increases as if new bud grows.

Carbohydrates and sugar increased by the enhanced efficiency of photosynthesis are sent to the roots as nutrients. Because the plant immunopotentiating composition and oxygen absorbed from the leaves are also transmitted to the roots through the trachea and conduit, the innate immunity of the plant root cells become more active to increase secreting antimicrobial enzymes antibacterial, antifungal, and antiviral substances. The secretion of antimicrobial will kill bacteria harmful to plants.

In addition, nutrients such as glucose are converted to organic acids as necessary, and secreted from the roots with acid and oxygen. The secreted organic acid increases soil bacteria which gather to seek nutrients such as amino acids and sugars and are useful to the plant, and the increased soil bacteria form a biofilm of thickness in the range from 10 to 100 microns which protects the plant roots. The organic acid that is secreted from the roots makes insoluble phosphorus, potassium, trace minerals existing in soil soluble to produce nutrients required for plants. It is known that these bacteria fix or decompose the nitrogen in air and the organic nitrogen in the soil and convert them into nutrient such as nitrate.

In other words, it may be seen that the plant roots of plants actively controls soil bacteria by secreting antimicrobial substances and nutrients such as oxygen and sugar for collecting bacteria. As flowers secrete nectar to attract bees, their roots have a mechanism of collecting bacteria beneficial to themselves.

The revived roots grow to spread themselves widely, seeking required nutrients. A plant may grow flowers, leaves, and stems, and fruits with phosphorus, potassium, nitrogen, and trace minerals obtained from the roots.

Namely, the plant immunopotentiating composition of the present invention stimulates plant's innate immune which contains the mechanism of apoptosis to activate the vacuole autophagy so that aged chloroplast and mitochondria are removed to accelerate the intercellular detoxification to revive the plant. This results in increasing photosynthesis and philological mechanism of the plant, and at the same time, the plant root secrets various substances including organic acid, sugar, amino acid, oxygen, and special decomposing enzymes in order to control soil bacteria for the plant for taking an advantage of them By using the plant immunopotentiating composition, the present invention enhances antimicrobial, antiviral, and antifungal activities due to the innate immune, and at the same time, increases photosynthesis significantly to accelerate the activity of mitochondria. The composition also develops strong roots to absorb nutrients from soil actively to enhance the bioactivity (or the physiological activity) of the plant. As a result, it is possible to significantly reduce the amount of fertilizer of nitrogen, phosphate, and potassium, and minerals necessary for plants which have been emphasized in conventional farming methods.

Unlike the organic farming method, the present invention may reduce the fertilizer such as nitrogen by virtue of the action of soil bacteria group. It is also possible to reduce the damage due to insect pests flying seeking a nitrogen content secreted from the leaves. In addition, by activating the innate immunity, it is also possible to control the soil bacteria by secretions from the roots, requiring no external artificial addition such as the EM bacteria.

Therefore, the farming method using the plant immunopotentiating composition moves away from the conventional farming methods of actively giving fertilizer and soil bacteria, to natural and enriched farming methods which enhance vitality so that plant roots may be developed by themselves for producing nutrition.

Furthermore, because the nutrient produced by the plants from soil may contain tiny amount of minerals such as zinc which the conventional fertilizers do not contain, the growth effect is enhanced to not only increase the yield but also add acidity and sweetness. Since the innate immunity increases, needless to say that the plants become strong against pests.

In addition, the present invention has significant advantages from a stand point of natural cultivation farming Natural cultivation farming refers to the farming methods which grow plants in symbiosis of many different plants, including weeds, in a way that the roots of weeds produce nutrients from the soil, which is then used to cultivate crops. The natural cultivation farming method is resistive to disease, does not attract pests because it does not absorb the nitrogen component excessively, the crops are stardy, and yet the taste of crops is good. However, because the yield is low while the farming method is time-consuming, the price of crops becomes high.

The cultivation farming method using the plant immunopotentiating component of the present invention may effectively grow crops, much similar to natural farming crops, in conventional fields and paddies, and yet significantly increase the yield compared with conventional farming methods including natural farming. The cultivation farming method using the plant immunopotentiating component of the present invention may also obtain plants that have herbicide tolerance or salinity tolerance.

The present inventors have discovered the salinity tolerance of papaya field when it was covered with flooded sea water caused by a typhoon. While many papaya plants were withered, papaya plants in the field sprayed the plant immunopotentiating compositions of the present invention were not damaged and obtained crops. Thereafter, in a salt damage desert land, the method according to the present invention was able to grow wheat. Furthermore, as shown in the following embodiments, tomatoes activated with the plant immunopotentiating components may be grown in a bucket without a hole while continuously spraying saltwater every day.

For this mechanism, it was discovered that the plant roots formed a high sodium ion gradient due to the sodium ion channel and the potassium ion channel in the cells of the roots. (J. Exp. Bot. 55, 939-949, Peng, Y. H., Zhu, Y. F., Mao, Y. Q., Wang, S. M., Su, W. A. and Tang, Z. C. (2004) "Alkali grass resists salt stress through high and an endodermis barrier to"). In addition, it was also reported that a biofilm of pores size in the range from 150 μm to 200 μm strongly hampered the entry of chlorine.

It may be attributed that the present invention enhances the action of inhibiting of sodium ion penetration by the transporter and the sodium pump of the plant root cells, and activates blocking the entry of unwanted chlorine ions by actively forming the biofilm formation by roots.

The method according to the present invention may be also used in fields covered with seawater due to typhoons or high tides, re-greed salt-damaged field due to desertification, and cultivation using seawater. In addition, the humidity retention power in the dry land and retention of humidity in a wide area of dessert are also discovered.

The present inventors have found that plants grown using the method according to the present invention has the herbicide resistance. When the plant immunopotentiating composition of the present invention was sprayed on weed in the footpath of rice field where herbicide had been already disseminated, the weed did not die. When the plant immunopotentiating composition of the present invention was sprayed on a golf course turf where high-concentration herbicide had been disseminated, the turf was not withered.

It was confirmed that the decomposition of the herbicide does not occur even if the plant immunopotentiating component of the present invention was mixed with herbicide. The immunopotentiating component of the present invention enhances the detoxification effect of vacuoles to obtain the herbicide. This has also been confirmed by the embodiments disclosed below.

The studies to date have discovered one mechanism of herbicide detoxification degradation in the plant vacuoles, showing that plants have the detoxification mechanism that results in the herbicide resistance. It is conjectured that the present invention evolves the herbicide resistance by activating the intracellular detoxification such as vacuolar autophagy and the mechanism of transferring the herbicide conjugate to vacuoles where a special breakdown enzyme decomposes the conjugate.

In the method according to the present invention, the herbicide includes simazine, atrazine and Roundup include, and a commonly available commercial herbicide may be used without particular limitation.

By successfully activating the innate immunity of plants by the plant immunopotentiating composition of the present invention, the plants have resistances fungi, viruses, or bacteria, yield crops competing with weeds and pests. Because the crops produced by the farming method according to the present invention have strong vitality (or the physiological activity), despite of the fact that the farming method is close to natural cultivation, the plant roots develop themselves deeply to secrete organic acids, sugars, oxygen, antimicrobial substances, and a special degrading enzyme. At the same time, it is possible to increase dramatically the yield by producing nutrients including mineral phosphorus, potassium or nitrogen, and mineral from the soil component in cooperation with the soil bacteria selected by the plants. In other words, the farming method according to the present invention may increase sugar, acidity, or umami with little fungicides, insecticides, herbicides and other chemicals, to yield mineral rich crops with high efficiency.

Because of the farming method according to the present invention is very much similar to natural cultivation, it allows inhibition of various biological organisms including algae, aquatic insects, and aquatic animals such as frogs, loach and snail. Furthermore, we were able recover a rich natural rural area where numerous dragonflies fly and a flock of herons visit from summer to autumn. That is, the method according to the present invention may also restore biodiversity, contributing to sustention of the global environment.

Because the farming method according to the present invention archives highly efficient farming to yield strong crops while competing with weeds, it does not require removing weeds completely although it is very close to natural cultivation. Furthermore, since the farming method is close to natural farming cultivation, it is possible to produce crops that contain nutritious including antioxidant nutrients and trace minerals. The fruit produced by the method according to the present invention, has more sugar and acidity and more taste of umami and flavor.

In the method according to the present invention, agricultural products or plant crops to be grown include rice, ancient rice such as black rice, green rice, and red rice, grains such as wheat, barley, oat, rye, oats, millet, Japanese millet, and corn, beans such as soybean, adzuki bean, cowpea, beans, peanuts, peas, Sora beans, lentils, chickpeas, and tamarin, leafy vegetables such as green onion, lettuce, cabbage, Chinese cabbage, spinach, Japanese mustard spinach, mizuna, Kikuna-Tacana, celery, scallions, Thailand Sai, and bok Choy, bud vegetable such as broccoli and cauliflower, bulb vegetables such as onion, garlic and shallots, root vegetables such as asparagus, kohlrabi, and bamboo shoots, seed vegetables such as cucumber, eggplant, tomato, Himan pumpkin, watermelon, melon, strawberry, and red pepper, stem vegetables such as radish, turnip, lotus root, carrot, burdock, wild yam, sweet potato, Japanese yam, and yam, fruits such as orange, apple, grapes, pear, peach, persimmon, cherry, mango, kiwi, banana, pineapple, papaya, blueberry, and avocado, teas, trees such as wisteria, azaleas, and magnolia Barra, flowers such as orchid, cosmos, chrysanthemum, Gloxinia, Yuri Bekonia Azalea, cyclamen, lily of the valley, tulip, zinnia, Margaret, geranium, calendula, gerbera, sweet pea, iris, carnation, Cymbidium, clematis, iris, African violet, and primrose, herbs such as marigold, lavender, sage, mint, thyme, Rosemary Fennell, Yarrow, lemon balm, saffron, chicory, basil oregano, St. John's Wort, Arca net, Aloe, and Ginger, medicine herbs such as bupleurum root, Japanese angelica root, peony, licorice, kudzu, ephedra, ginger, Houttuynia, Angelica keiskei, Epimedium, Japanese knotweed, Prunella vulgaris, plantain, cocklebur, Gama, mugwort, Pueraria lobata, bellflower, Geranium thunbergii, Ophiopogon japonicus, horsetail, violet, Swertia japonica, dandelion, Tsuruna-crested, Japanese silver leaf, chickweed, saxifrage, and gentian, but they are not particularly limited if plants can be generally grown.

Farming may be adopted in various forms including field crops, rice paddies, water and natural hydroponics cultivation, greenhouse cultivation, and kitchen vegetable garden.

The immunopotentiating composition as an embodiment of the present invention may be mixed with soil and fertilizer. In this case, conventional soil and fertilizer are not limited particularly if they are appropriate for growing various plants. As described above, the plant immunopotentiating composition of the present invention is applicable to growing various plants, and hence it may also be a plant cultivation kits with seeds of various plants, where plant seeds are preferably seeds of plants to which plant immunopotentiating composition of the present invention may be applicable.

EXAMPLE

Example 1

Rice

Two surfaces of rice nursery were prepared, conventional rice hulls of the Kishihikari-brand were spread on one of the surface while those soaked in the plant immune potentiating composition diluted 200 times was sprayed on the other surface. When the seedlings grew about 10 cm in the nursery, and the plant immunopotentiating composition diluted to 300 times was sprayed on to the surface of seedlings that had been treated with the plant immunopotentiating composition. The grown seedlings were planted in 2 similar rice fields adjacent to each other, and the undiluted solution of the plant immunopotentiating composition was poured into the field of the seedlings grown with the immunopotentiating composition at a rate of 20 L per tan. The rice field without the immunopotentiating composition was cultivated conventionally. Every other week, the plant immunopotentiating composition diluted by 500 times was sprayed on the rice field with the immunopotentiating composition, and at heading, the undiluted solution of the plant immunopotentiating composition is poured into the field with the immunopotentiating composition at a rate of 20 L per tan. After heading, the plant immunopotentiating composition diluted 200 times was sprayed twice before harvest.

As a result, while the conventional crop was as shown in FIG. 1a, rice with plant immunity enhancing composition are often larger grain of rice ears hanging long as shown in FIG. 1b. As seen from the figure, leaves treated with the immunopotentiating composition lush and even in the time of harvest they were outstanding, showing full of vitality. When the rice milled and steamed, the steamed rice exhibited rich glutinous feeling.

In addition, the stem of the rice treated with the plant immunopotentiating composition were large and the roots also extended deep underground breaking through the hard soil.

The comparative table below shows the "number of segregations," the "number of rice grains per stem," and the "yield per stock" of rice using the conventional method and the plant immunopotentiating composition.

TABLE 2

| Stock No. | No. of segregations | | No. of rice grains per ear | | Yield per stock | |
|---|---|---|---|---|---|---|
| | Conventional | MRE | Conventional | MRE | Conventional | MRE |
| (1) | 19 | 28 | 102 | 158 | 1,938 | 4,424 |
| (2) | 19 | 23 | 137 | 138 | 2,603 | 3,174 |
| (3) | 20 | 29 | 123 | 143 | 2,460 | 4,147 |
| (4) | 20 | 26 | 95 | 145 | 1,900 | 3,770 |
| (5) | 19 | 24 | 108 | 148 | 2,052 | 3,552 |
| Mean | 29.4 | 26.0 | 113.0 | 146.4 | 2191 | 3813 |
| Standard Deviation | 0.55 | 2.55 | 16.93 | 7.44 | 320 | 491 |
| Increasing rate | | 1.34 | | 1.29 | | 1.74 |

Comparing with the rice using the conventional framing method, the rise using the immunopotentiating composition is 1.34 times more for the number of segregations, 1.29 times more for the number of rice grains per ear, and 1.74 time more for the yield. Zinc is an essential ingredient to out body. Brown rice of the conventional farming method has 18 mg of zinc while brown rice of the farming method using the immunopotentiating composition has 2.7 mg indicating significant increase.

Example 2

Sweet Potato

Two pieces of sweet potatoes as shown in FIG. 2a were grown, and the plant immunopotentiating composition (the MRE fermentation solution) diluted 300 times was sprayed onto the one of the right once every 3 days. Digging the roots showed that the one grown with the immunopotentiating composition clearly developed more.

Example 3

Blooming 1

Million Gold

Two seedlings Million Gold were grown as shown in FIG. 3a. The plant immunopotentiating composition (the MRE fermentation solution) diluted 300 times was sprayed once every 3 days. FIGS. 3b and 3c are the same plant with different angles, and they clearly show more flowers and leaves.

Example 4

Blooming 2

Gloxinia

Figure 4A:
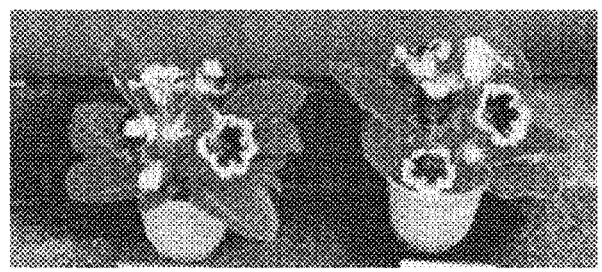
FIG. 4 is a photograph to compare the development of gloxinia with and without using the plant immunopotentiating composition in an embodiment of the present invention.
Figure 4B:
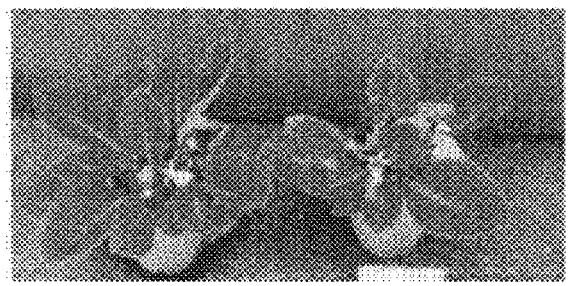
Figure 4C:

Two potted Gloxinia in full bloom shown in FIG. 4 were procured to use. Flowers end soon, and the Gloxinia dis not bloom any more as shown in FIG. 4b. The plant immunopotentiating composition (the MRE fermentation solution) diluted 300 times was sprayed onto the left pot once every 3 days. As a result, the left pot using the plant immunopotentiating composition bloomed again while the right does not. The Gloxinia of the right {sic: left} pot repeated blooming more than 3 times Example 5

Mandarin Orange

A mandarin orange tree grown in Fruit of three or four every year became the tree of orange growing in a sterile had 3 to 4 pieces of orange every year but they were dried without moisture. The plant immunopotentiating composition (the MRE fermentation solution) diluted 200 times was sprayed onto leaves and stem once every 3 weeks. As a result, 22 pieces of delicious sweet orange were obtained without giving any fertilizer.

Example 6

Sugar Content of Mini Tomato

Ten similar seedlings of mini tomato were placed in the bucket for growing them in a greenhouse. For contrast, 5 seedlings were grown using the conventional method while the other 5 seedlings were grown by spraying the plant immunopotentiating composition diluted 300 times every day. As a result, there was clear increase in the sugar content. The acidity also increased. The mini tomato grown with the method of the present invention clearly tasted better because of the sugar content and the acidity.

TABLE 3

| Conventional farming | | Farming of present invention (Innate immunity activation farming) | |
|---|---|---|---|
| | Sugar content | | Sugar content |
| (1) | 8.2 | A | 10.5 |
| (2) | 8.6 | B | 9.8 |
| (3) | 7.9 | C | 10.9 |
| (4) | 8.4 | D | 11.4 |
| (5) | 9.1 | E | 10.3 |

Example 7

Apple

The plant immunopotentiating composition (the MRE fermentation solution) diluted 200 times was sprayed on leaves and trunk of an apple tree after blooming, pollination, and ripening. Then, before harvest, the diluted composition was sprayed once every 2 to 3 weeks. As a result, the sugar content of the apple significantly increased compared with the conventional method. What is more, the tree also became stronger.

Example 8

Green Onion

Green onion was attempted to grow in a land where leaf rust occurs due to continuous cropping. The green onion does not grow well due to the continuous cropping. After budding, the plant immunopotentiating composition (the MRE fermentation solution) diluted 200 times was sprayed widely once every other week. As a result, although green onion is small and thin before spraying, it becomes larges and thicker, hardly observing leaf rust.

Example 9

Lotus Root

The plant immunopotentiating composition (the MRE fermentation solution) diluted 2000 times was poured into a pond of lotus. After that, the plant immunopotentiating composition (the MRE fermentation solution) diluted 300 times was sprayed onto leaves of the lotus once every other week. The lotus became larger and better, spreading many thin and long roots. The taste of the lotus did not change.

Example 10

Saline Tolerance

Four seedlings of mini tomato were grown in separate plastic buckets with no holes. When they grow to 40 cm height, 2 of them were selected to spray plant immunopotentiating composition (the MRE fermentation solution) diluted 300 times widely every day. After some blooming, 500 mL of sea water was poured into each bucket. The tomato without spraying the immunopotentiating composition died while the ones with the immunopotentiating composition produced crops. These tomatoes were not different in their size and quantity from the ones grown separately using the plant immunopotentiating composition.

Example 11

Herbicide Tolerance

The plant immunopotentiating composition diluted by 30 times was used to conduct an experiment of the herbicide tolerance. Atrazine of concentration 50% and simazine of concentration 50% were mixed and adjusted to make an ordinary herbicide which was then sprayed onto lawn planted in 2 planters. After 30 minutes, the immunopotentiating composition diluted 30 times was sprayed onto one of the planters. As a result of examining the condition after 24 hours, the lawn sprayed the plant immunopotentiating composition was very much green being in affected while the lawn without the plant immunopotentiating composition changes its color. On the $7^{th}$ days, the lawn with the plant immunopotentiating composition was still healthy while the one without the composition completely withers.

Example 12

Agricultural Chemical and Herbicide Tolerance

Tree of summer tangerine weakened because of continued application of pesticide, in the state of dieback on the verge, as half of the stem up to height about 1.2 m was rotten from the stem base was missing. The tree barely bore a single fruit. The plant immunopotentiating composition diluted by 500 times was sprayed onto leaves, stems, and roots once a week for 10 months. As a result, the stem was revived, appears more healthy leaves, bearing 12 pieces of large summer tangerine.

Example 13

Okura

Okara tree grown according to the present invention became significantly larger, and harvest continued until October beyond an ordinary harvest time.

Example 14

Azuki Bean and Sasagi

"Azuki bean" and "Sasagi" grown with the farming method of the present invention became large. There was much harvest and the roots were spread more than those with the conventional method.

Example 15

Green Soybean

Sheath become Green soybeans (soybean) grown by the method according to the present invention had larger sheath. Its roots spread widely and strongly.

Example 16

Taro

Taro grown with the method of the present invention became larger than those grown with the conventional method.

Example 17

Potato

Potato grown with the method of the present invention became larger than those grown with the conventional method.

Example 18

Snack Pea

Tree of snack pea grown with the method of the present invention became thicker and bore larger peas for a longer time.

Example 19

Sweet Pepper

Sweet pepper grown with the method of the present invention bore lager and more peppers. It bore peppers even after the second half of December.

Example 20

Others

The method according to the present invention resulted in more crops of larger and better taste of green onion, cucumber, eggplant, purple vine greens, bitter gourd, persimmon, ginger, butterbur, plum, blueberry, Popo, red pepper, radish, turnip, broccoli, mizuna, Chinese cabbage, and broad beans. Their roots developed stringer and became resistant to pests.

Example 21

Production of the Plant Immunopotentiating Composition (the MRE Fermentation Solution)

A general method for culturing aerobic gram-positive bacteria was applied to culture MRE symbiotic bacteria group. Aeration through a culture aeration tank of volume 1.2 m$^3$ filled with 1000 L of water was conducted. As nutrients, 3 kg of fish meal, 3 kg of rice bran, 1.6 kg of oil cake, and 350 g of gravy were added to the culture aeration tank, and appropriate amounts of minerals such as silica and magnesium sulfate were also added. The fungus body was placed into the tank to culture it with aeration under the following condition: the culture pH in the range from 6.0 to 6.8; the tank temperature in the range from 25° C. to 35° C.; and the dissolved oxygen concentration in the range from 0.5 mg/L to 1.2 mg/L.

After obtaining sufficient growth and stabilization of bacteria, the plant was left in starvation without any nutrition to MRE symbiotic bacteria group, and aeration was continued at temperature in the range from 15 to 35° C., and then depletion of the nitrogen component triggered sporulation of MRE symbiotic bacteria group. Once the culture solution became transparent, stopping the aeration (supplying oxygen supply) started precipitation of spores at once to become a clear supernatant solution.

The supernatant thus obtained in this manner was further filtered with a membrane of pore size 0.2 μm to obtain MRE decomposition solution which contains the immunopotentiating substance. The timing to stop the aeration maybe determined by confirming the completion of spores with a phase contrast microscope.

It addition, needless to say, the present invention may be modified in various ways, and is not limited by the Examples described above without changing the scope of the invention for further modifications.

What is claimed is:

1. A method for growing a plant which has enhanced immunity or physiological activity to internal or external stress, comprising:
   a step of applying a plant immunopotentiating composition that is formed through cell lysis associated with spore formation of spore aerobic bacteria to the plant, wherein
   the plant immunopotentiating composition is obtained by steps of: (1) incubating the spore aerobic bacteria under a condition suitable for growth, (2) placing a resultant culture medium under a starvation condition, thereby causing the bacteria to internally sporulate, and (3) removing from said culture medium impurities containing said internally sporulated bacteria, and
   the spore aerobic bacteria is a symbiotic bacterium group consisting of *Bacillus* sp. FERM BP-11209, *Lysinibacillus fusiformis* FERM BP-11206, *Bacillus sonorensis*, *Lysinibacillus* sp. FERM BP-11207, and *Comamonas* sp. FERM BP-11208.

2. The method according to claim 1, wherein
   the step of applying is spraying the plant immunopotentiating composition on either soil or cultivation medium for plants so that the immunopotentiating composition is absorbed by plant roots.

3. The method according to claim 1, wherein
the step of applying is applying the plant immunopotentiating composition onto the leaves of the plant.

4. The method according to claim 1, wherein
the plant acquires a trait selected from a group consisting of anti-pathogenic activity, anti-pest activity, salt tolerance, and herbicide resistance.

5. The method according to claim 1, wherein
the internal or external stress is selected from a group consisting of pathogenic, pests, viruses, high concentration of salt, strong light, ultraviolet radiation, high temperature, low temperature, dryness, heavy metals, and air-polluting gas.

6. The method according to claim 1, wherein the plant is selected from a group consisting of leafy vegetables, flower bud vegetables, bulb vegetables, stem vegetables, seed vegetables, root vegetables, plants which give beans or grain, plants which give fruits, plants which give ornamental flowers, and medical plants.

7. The method according to claim 6, wherein
the plant is selected from a group consisting of rice, sweet potato, Million Gold, Gloxinia, orange, mini tomato, apple, Japanese leek onion, lotus root, okra, red bean, Sasagi, soybean, taro, potato, snack pea, green pepper, green onion, cucumber, eggplant, purple vine vegetable, bitter gourd, persimmons, ginger, butterbur, plum, blueberry, Popo, pepper, radish, turnip, broccoli, mizuna, Chinese cabbage, and broad bean.

8. The method according to claim 1, wherein
the plant immunopotentiating composition is diluted in the range from 100 to 1000 times.

9. The method according to claim 1, wherein
the step of the applying is carried out once every 1 to 3 weeks.

10. The method according to claim 1, wherein
the plant is grown in a form selected from a group consisting of upland, paddy, hydroponics, natural cultivation, and greenhouse cultivation.

* * * * *